US006310229B1

(12) United States Patent
Soloveichik et al.

(10) Patent No.: US 6,310,229 B1
(45) Date of Patent: Oct. 30, 2001

(54) LEAD HALOPHENOXIDES AND CARBONYLATION CATALYST AND METHOD FOR PREPARING AND EMPLOYING THEM

(75) Inventors: Grigorii Lev Soloveichik, Latham; Ben Purushatom Patel, Albany; John Yaw Ofori, Niskayuna, all of NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/466,030

(22) Filed: Dec. 20, 1999

(51) Int. Cl.[7] ............................. C07F 7/24; C07C 69/96; B01J 31/00
(52) U.S. Cl. ..................... 556/83; 502/171; 556/108; 558/270; 558/271; 558/274
(58) Field of Search ..................... 558/270, 271, 558/274; 556/83, 108; 502/178

(56) References Cited

U.S. PATENT DOCUMENTS 5,498,789  3/1996  Takagi et al. ................. 558/270
5,726,340  3/1998  Takagi et al. ................. 558/274

FOREIGN PATENT DOCUMENTS 663388    7/1995   (EP) .
2311777   10/1997  (GB) .
40541     7/2000   (WO) .

OTHER PUBLICATIONS

International Search Report (Feb. 2001).

Primary Examiner—Porfirio Nazario-Gonzalez
(74) Attorney, Agent, or Firm—Noreen C. Johnson; Christian G. Cabou

(57) ABSTRACT

Lead halophenoxides, especially bromophenoxides, are prepared by the reaction of lead(II) oxides with a hydroxyaromatic compound such as phenol and a chloride or bromide salt such as an alkali metal bromide, a tetraalkylammonium bromide or a bexaalkylguanidinium bromide. They are useful in catalyst compositions for the oxidative carbonylation of hydroxyaromatic compounds to diaryl carbonates.

39 Claims, No Drawings

LEAD HALOPHENOXIDES AND CARBONYLATION CATALYST AND METHOD FOR PREPARING AND EMPLOYING THEM

BACKGROUND OF THE INVENTION

This invention relates to the preparation of diaryl carbonates by carbonylation. More particularly, it relates to the improvement of diaryl carbonate yield and selectivity in the carbonylation reaction.

Diaryl carbonates are valuable intermediates for the preparation of polycarbonates by transesterification with bisphenols in the melt. This method of polycarbonate preparation has environmental advantages over methods that employ phosgene, a toxic gas, as a reagent and environmentally detrimental chlorinated aliphatic hydrocarbons such as methylene chloride as solvents.

Various methods for the preparation of diaryl carbonates by an oxidative carbonylation (hereinafter sometimes simply "carbonylation" for brevity) reaction of hydroxyaromatic compounds with carbon monoxide and oxygen have been disclosed. In general, the carbonylation reaction requires a rather complex catalyst. Reference is made, for example, to U.S. Pat. No. 4,187,242, in which the catalyst is a heavy Group VIII metal; i.e., a Group VIII metal having an atomic number of at least 44, said metals consisting of ruthenium, rhodium, palladium, osmium, iridium and platinum, or a complex thereof.

The production of carbonates may frequently be improved by including a lead-containing cocatalyst along with the heavy Group VIII metal catalyst. Suitable lead-containing cocatalysts have been described broadly in various patents and publications, particularly in U.S. Pat. No. 5,498,789. Also preferred in general is the use of various halides, as illustrated by tetra-n-butylammonium bromide, as part of the catalyst package. Compounds characterized as inert solvents, such as toluene, diethyl ether, diphenyl ether and acetonitrile, can also be present.

Lead-containing systems of this type have, however, certain disadvantages. In the first place, selectivity of the reaction (i.e., the amount of diphenyl carbonate produced as a percentage of total reaction products derived from phenol) is poor, with various by-products such as biphenols and bromophenols being formed in addition to the desired diaryl carbonates. In the second place, sediments are often formed when lead compounds such as lead(II) oxide are added to other components of the catalyst package, and their presence can result in poor reproducibility of reaction results. In the third place, water is frequently formed by the reaction of lead(II) oxide with the other catalyst components and may adversely affect the activity of the catalyst.

It is of interest, therefore, to develop lead-containing catalyst systems that do not adversely affect catalyst activity.

SUMMARY OF THE INVENTION

The present invention is based on the discovery that lead(II) oxide reacts with hydroxyaromatic compounds such as phenol in the presence of halide salts, forming lead halophenoxides (including lead oxyhalophenoxides) which form homogeneous mixtures with other carbonylation catalyst constituents. Said lead halophenoxides, when present in the catalyst system, afford diaryl carbonate with improved selectivity and in high yield.

In one of its aspects, an embodiment of the invention is directed to lead halophenoxides of the formula $$Pb_nO_m(OA)_{(2-z)(n-m)}X_{z(n-m)},\qquad\text{(I)}$$

wherein A is an aromatic radical, X is chlorine or bromine, n has a value in the range of 1–3, m has a value in the range of 0–1 and z has a value in the range of 0.1–2.0, with the proviso that the values of n and m cannot be the same.

A further aspect of the invention is directed to a method for preparing a lead halophenoxide. An embodiment of the method comprises contacting lead(II) oxide with at least one bromide or chloride salt and at least one hydroxyaromatic compound, the molar ratio of lead to bromide or chloride being at least 2:1.

A further aspect is directed to a method for preparing a diaryl carbonate. An embodiment of the method comprises contacting at least one hydroxyaromatic compound with oxygen and carbon monoxide in the presence of an amount effective for carbonylation of a catalyst composition comprising the following and any reaction products thereof:

(A) a Group VIII metal having an atomic number of at least 44 or a compound thereof, (B) at least one bromide or chloride salt, and (C) at least one lead halophenoxide, particularly one of formula I.

A still further aspect is directed to catalyst compositions comprising components A, B and C as described above, and any reaction products thereof.

DETAILED DESCRIPTION OF PREFERRED EMBODIMENTS

In formula I, A may be any aromatic radical, unsubstituted or substituted. In general, A corresponds to the diaryl carbonate to be formed in the carbonylation reaction. Therefore, it is usually unsubstituted phenyl. X may be bromide or chloride and is preferably bromide.

The values of n, m and z are as described hereinabove. Most often, n is 2.5–3 and m is 0.8–1.

The method of the invention for the preparation of the lead halophenoxides involves bringing the designated reagents into contact, usually at a temperature in the range of about 20–120° C. Suitable bromide and chloride salts include alkali metal and alkaline earth metal bromides and chlorides and tetraalkylammonium, tetraalkylphosphonium and hexaalkylguanidinium bromides and chlorides. The bromides are preferred. When the bromide or chloride salt is an inorganic salt such as sodium bromide, the reaction is preferably facilitated by the presence of an electron-donating compound, especially a nitrile such as acetonitrile or a polyether such as diethylene glycol dimethyl ether (diglyme) or tetraethylene glycol dimethyl ether (tetraglyme).

The molar ratio of lead to halide in the reaction mixture should be at least 2:1, since at lower molar ratios the principal products are the lead(II) halides and hydroxyhalides. In general, molar ratios in the range of about 2–20:1 are preferred. It should be noted, however, that the molar ratio of lead to halide in the product is not necessarily at least 2:1. Rather, the method of the invention involves this minimum since it permits isolation of the lead halophenoxide.

Hydroxyaromatic compound is most often present in excess and is preferably employed as a solvent for the reaction. The electron-donating compound, when employed, may also be present in molar excess with respect to halide salt, typically in a molar ratio in the range of about 50–200:1. Under such conditions, the lead halophenoxide forms a separate phase, which may be isolated by conventional methods including such operations as filtration and drying.

Any hydroxyaromatic compound may be employed in the diaryl carbonate preparation method of the present invention. Monohydroxyaromatic compounds, such as phenol, the cresols, the xylenols and p-cumylphenol, are generally preferred with phenol being most preferred. The invention may, however, also be employed with dihydroxyaromatic compounds such as resorcinol, hydroquinone and 2,2-bis(4-hydroxyphenyl)propane or "bisphenol A", whereupon the products are polycarbonate oligomers.

Other reagents in the diaryl carbonate preparation method of the invention are oxygen and carbon monoxide, which react with the phenol to form the desired diaryl carbonate. They may be employed in high purity form or diluted with another gas such as nitrogen, argon or carbon dioxide, which has no negative effect on the reaction.

For the sake of brevity, the constituents of the catalyst system of the invention are defined as "components" irrespective of whether a reaction between said constituents occurs before or during the carbonylation reaction. Thus, the catalyst system may include said components and any reaction products thereof.

Component A of the catalyst system is one of the heavy Group VIII metals, preferably palladium, or a compound thereof. Thus, useful palladium materials include elemental palladium-containing entities such as palladium black, palladiun/carbon, palladium/alumina and palladium/silica; palladium compounds such as palladium chloride, palladium bromide, palladium iodide, palladium sulfate, palladium nitrate, palladium acetate and palladium 2,4-pentanedionate; and palladium-containing complexes involving such compounds as carbon monoxide, amines, nitriles, phosphines and olefins. Preferred in many instances are palladium(II) salts of organic acids, most often $C_{2-6}$ aliphatic carboxylic acids, and palladium(II) salts of β-diketones. Palladium(II) acetate and palladium(II) 2,4-pentanedionate, especially the latter, are generally most preferred. Mixtures of the aforementioned palladium materials are also contemplated.

Component B is at least one bromide or chloride salt. It may be an alkali metal or alkaline earth metal halide, preferably a bromide such as lithium bromide, sodium bromide, potassium bromide, calcium bromide or magnesium bromide. It may also be a quaternary ammonium or quaternary phosphonium salt such as tetramethylammonium bromide, tetraethylammonium bromide, tetra-n-butylammonium bromide or tetramethylphosphonium bromide, or a hexaalkylguanidinium salt such as hexaethylguanidinium bromide.

Component C is at least one lead halophenoxide. It is preferably a compound of formula I and especially a lead bromophenoxide of that formula. Halophenoxides are included in the carbonylation catalyst system in catalytic amounts. In this context a "catalytic amount" is an amount of halophenoxide (or combination of halophenoxides) that increases the number of moles of diaryl carbonate produced per mole of Group VIII metal utilized; increases the number of moles of diaryl carbonate produced per mole of halide utilized; or increases selectivity toward diaryl carbonate production beyond that obtained in the absence of the halophenoxide (or combination of halophenoxides). Optimum amounts of a halophenoxide in a given application will depend on various factors, such as the identity of reactants and reaction conditions.

In addition to the aforementioned reactants and catalyst system, a desiccant can be present in the reaction system. Preferred desiccants include non-reactive materials such as molecular sieves, as illustrated by 3-Åangstrom (hereinafter "3A") molecular sieves. They are usually isolated from the other reactants, as by presence in a basket mounted to a stirrer shaft or the like.

Component A is most often present in the amount of about 0.1–10,000 ppm by weight of the appropriate Group VII metal (usually palladium), based on hydroxyaromatic compound, and component B in the amount of about 1–2,000 equivalents of halide per equivalent of the Group VIII metal of component A. Component C is generally present in the amount of about 0.2–200 gram-atoms of lead per equivalent of the Group VIII metal of component A.

The method of the invention is preferably conducted in a reactor in which the hydroxyaromatic compound and catalyst system are charged under pressure of carbon monoxide and oxygen and heated. The reaction pressure is most often within the range of about 1–500 and preferably about 1–150 atm. Gas is usually supplied in proportions of about 1–50 mole percent oxygen with the balance being carbon monoxide and optionally one or more inert gases, and in any event outside the explosion range for safety reasons. The gases may be introduced separately or as a mixture. Reaction temperatures in the range of about 60–150° C. are typical. It is often preferred to maintain a substantially constant gas pressure and partial pressure of carbon monoxide and oxygen, as described, for example, in U.S. Pat. No. 5,399,734, until conversion of the hydroxyaromatic compound is complete.

The diaryl carbonates produced by the method of the invention may be isolated by conventional techniques. It is often preferred to form and thermally crack an adduct of the diaryl carbonate with the hydroxyaromatic compound, as described in U.S. Pat. Nos. 5,239,106 and 5,312,955.

Certain exemplary embodiments of the invention are illustrated by the following, non-limiting Examples. All percentages are by weight unless otherwise designated. Minor variations in reagent amounts from one example to another in Examples 9–13 are not believed significant from the standpoint of yield and selectivity to diphenyl carbonate.

EXAMPLES 1–6

Various proportions of tetra-n-butylammonium bromide (TBAB) or hexaethylguanidinium bromide (HEGB) and phenol (PhOH) were combined with lead(II) oxide (PbO) and the resulting mixtures were stirred overnight at 70° C. After cooling to room temperature, the solid precipitates were removed by filtration, washed twice with acetonitrile and dried in a vacuum oven at 100° C.

EXAMPLES 7–8

Lead(II) oxide (PbO), 2.715 g, was dissolved in 10 ml of phenol (PhOH) at 100° C. and the resulting solution was added to various amounts of sodium bromide suspended in a mixture of 5 ml of phenol and 5 ml of acetonitnile (ACN). The resulting mixtures were stirred overnight at 100° C. After cooling to room temperature, the solid precipitates, which were the desired lead bromophenoxides, were removed by filtration, washed twice with acetonitrile and dried in a vacuum oven at 100° C.

In each example, the desired lead bromophenoxide was formed. The products were shown by X-ray diffraction to be discrete compounds, rather than mixtures of such compounds as lead oxide, lead phenoxide and lead bromide. The proportions and analyses applicable to the products of Examples 1–8 are given in Table I.

TABLE I

| Example | 1 | 2 | 3 | 4 | 5 | 6 | 7 | 8 |
|---|---|---|---|---|---|---|---|---|
| Bromide: | | | | | | | | |
| Identity | TBAB | TBAB | HEGB | HEGB | HEGB | HEGB | NaBr | NaBr |
| Amount, mg | 570 | 2,850 | 540 | 510 | 570 | 155 | 150 | 75 |
| PbO, mg | 1,000 | 5,030 | 1,000 | 1,800 | 2,500 | 1,800 | 2,700 | 2,700 |
| Molar ratio, Pb/Br | 2.5 | 2.55 | 2.55 | 4.4 | 6.8 | 16.0 | 8.3 | 16.6 |
| Solvent: | | | | | | | | |
| Identity | PhOH | PhOH | PhOH | PhOH | PhOH | PhOH | PhOH/ACN | PhOH/ACN |
| Amount, ml | 10 | 50 | 10 | 10 | 10 | 10 | 20 | 20 |
| Yield, %* | 62.0 | 44.0 | 65.7 | 68.0 | 49.7 | 38.8 | 36.1 | 87.8 |
| Br, % | 8.0 | 8.8 | 8.3 | 5.2 | 5.4 | 2.1 | 6.3 | 1.4 |
| Pb, % | 62.9 | 61.8 | 63.5 | 62.0 | 60.9 | 58.7 | 60.3 | 58.6 |

*Based on PbO.

EXAMPLES 9–10

Pressure-resistant reactors were charged in each example with 61.288 g (651 mmol) of phenol, 5 mg of palladium (26 ppm based on phenol) as palladium(II) 2,4-pentanedionate, 300 mg of lead bromophenoxide and various amounts of tetraethylammonium bromide. 3A molecular sieves, 38 g, were placed in a perforated polytetrafluoroethylene basket mounted to the stir shaft of each reactor.

The reactors were sealed, pressurized to 88.4 atm with a mixture of 90.5% (by volume) carbon monoxide and 9.5% oxygen and heated over 10 minutes to 100° C., with stirring. Heating at this temperature and stirring were continued for three hours, with periodic sampling. Diphenyl carbonate yields were evaluated in terms of "turnover number"; i.e., the number of moles of diaryl carbonate formed per gram-atom of palladium present. Also determined were selectivity and the percentage by weight of by-product bromophenols in the product mixture. Comparison was made with Control 1 in which the lead bromophenoxide was replaced with an equivalent amount of lead(II) oxide.

EXAMPLES 11–13

Pressure-resistant reactors were charged in each example with 61.1 g (653 mmol) of phenol, 5 mg of palladium(II) 2,4pentanedionate (26 ppm palladium based on phenol) as, 350 mg of lead bromophenoxide and various amounts of tetraethylammonium bromide. 3A molecular sieves, 38 g, were placed in a perforated polytetrafluoroethylene basket mounted to the stir shaft of each reactor.

The reactors were sealed, pressurized to 89.8 atm with a mixture of 90.9% (by volume) carbon monoxide and 9.1% oxygen and heated over 10 minutes 100° C., with stirring. Heating at this temperature and stirring were continued for three hours, with a mixture of 91% carbon monoxide and 9% oxygen being passed into the reactors at 330 sccm (standard cubic centimeters per minute) for the entire period. The reaction mixtures were sampled periodically as in Examples 9–10; comparison was made with Control 2 in which the lead bromophenoxide was replaced with an equivalent amount of lead(II) oxide.

The results of Examples 9–13 are given in Table II.

TABLE II

| Example | 9 | 10 | Control 1 | 11 | 12 | 13 | Control 2 |
|---|---|---|---|---|---|---|---|
| Lead bromophenoxide example | 7 | 2 | — | 1 | 4 | 6 | — |
| Total molar ratio, Br/Pd | 490 | 320 | 475 | 495 | 485 | 480 | 475 |
| Diphenyl carbonate, % | 33.3 | 35.6 | 27.5 | 36.0 | 34.8 | 34.0 | 27.7 |
| Turnover no. | 6,830 | 6,570 | 4,920 | 6,450 | 6,580 | 6,305 | 5,120 |
| Selectivity, % | 82.7 | 72.1 | 65.1 | 84.4 | 77.0 | 75.1 | 66.8 |
| Bromophenols, % | 1.25 | 1.0 | 1.55 | 1.1 | 1.4 | 1.4 | 1.4 |

It is apparent from Table II that the presence of the lead bromophenoxides of the present invention in the catalyst mixture improves yield of diphenyl carbonate and selectivity, and results in the formation of minimal proportions of by-product bromophenols.

It will be understood that each of the elements described above, or two or more together, may also find utility in applications differing from the types described herein. While the invention has been illustrated and described as embodied in a catalyst composition and method for producing diaryl carbonates using halophenoxides, it is not intended to be limited to the details shown, since various modifications and substitutions can be made without departing in any way from the spirit of the present invention. For example, additional effective IOCC compounds can be added to the reaction. As such, further modifications and equivalents of the invention herein disclosed may occur to persons skilled in the art using no more than routine experimentation, and all such modifications and equivalents are believed to be within the spirit and scope of the invention as defined by the following claims.

What is claimed is:

1. A lead haloaryloxide of the formula

$$Pb_nO_m(OA)_{(2-z)(n-m)}X_{z(n-m)}, \quad (I)$$

wherein A is an aromatic radical, X is chlorine or bromine, n has a value in the range of 1–3, m has a value in the range of 0–1 and z has a value in the range of 0.1–2.0, with the proviso that the values of n and m cannot be the same.

2. The lead haloaryloxide of claim 1, wherein X is bromine.

3. The lead haloaryloxide of claim 2, wherein A is unsubstituted phenyl.

4. The lead haloaryloxide of claim 2, wherein n is 2.5–3 and m is 0.8–1.

5. A lead halophenoxide of the formula $Pb_nO_m(OC_6H_5)_{(2-z)(n-m)}Br_{z(n-m)}$,
wherein n has a value in the range of 2.5–3, m has a value in the range of 0.8–1 and z has a value in the range of 0.1–2.0.

6. A method for preparing a lead haloaryloxide which comprises contacting lead(II) oxide with at least one bromide or chloride at least one hydroxyaromatic compound, the molar ratio of lead to bromide or chloride being at least 2:1.

7. The method of claim 6, wherein a bromide salt is employed.

8. The method of claim 7, wherein the bromide salt is a tetraalkylammonium bromide, tetraalkylphosphonium bromide or hexaalkylguanidinium bromide.

9. The method of claim 7, wherein the bromide salt is an alkali metal bromide and there is also present an electron-donating compound.

10. The method of claim 9, wherein the electron-donating compound is a nitrile or a polyether.

11. The method of claim 10, wherein the nitrile is acetonitrile.

12. The method of claim 7, wherein a temperature in the range of about 50–120° C. is employed.

13. A method for preparing a lead bromophenoxide which comprises contacting lead(II) oxide with a tetraalkylammonium bromide, tetraalkylphosphonium bromide or hexaalkylguanidinium bromide and phenol; the molar ratio of lead to bromide being in the range of about 2–20:1 and said phenol being employed as a solvent.

14. A method for preparing a lead bromophenoxide which comprises contacting lead(II) oxide with an alkali metal bromide, acetonitrile and phenol; the molar ratio of lead to bromide being in the range of about 2–20:1, said phenol being employed as a solvent and the molar ratio of said acetonitrile to said alkali metal bromide being in the range of about 50–200:1.

15. A method for preparing a diaryl carbonate, said method comprising the step of contacting at least one hydroxyaromatic compound with oxygen and carbon monoxide in the presence of a carbonylation catalyst system comprising a catalytic amount of at least one haloaryloxide.

16. The method of claim 15, wherein the carbonylation catalyst system further comprises catalytic amounts of the following components and any reaction products thereof:
(A) a Group VIII metal having an atomic number of at least 44 or a compound thereof and
(B) at least one bromide or chloride salt.

17. The method of claim 16, wherein the haloarloxide has the formula $$Pb_nO_m(OA)_{(2-z)(n-m)}X_{z(n-m)}, \quad (I)$$
wherein A is an aromatic radical, X is chlorine or bromine, n has a value in the range of 1–3, m has a value in the range of 0–1 and z has a value in the range of 0.1–2.0, with the proviso that the values of n and m cannot be the same.

18. The method of claim 17, wherein X is bromine.

19. The method of claim 17, wherein A is unsubstituted phenyl.

20. The method of claim 17, wherein the hydroxyaromatic compound is phenol.

21. The method of claim 17, wherein the Group VIIIB metal in component A is palladium.

22. The method of claim 21, wherein component A is palladium(II) 2,4-pentanedionate.

23. The method of claim 17, wherein component B is a bromide salt.

24. The method of claim 23, wherein component B is an alkali metal or alkaline earth metal bromide, a tetraalkylammonium bromide, a tetraalkylphosphonium bromide or a hexaalkylguanidinium bromide.

25. The method of claim 17, wherein a desiccant is also present.

26. The method of claim 17, wherein component A is present in the amount of about 0.1–10,000 ppm of Group VIIIB metal based on hydroxyaromatic compound, component B in the amount of about 1–2,000 equivalents of halide per equivalent of the Group VII metal of component A and component C in the amount of about 0.2–200 gram-atoms of lead per equivalent of the Group VIII metal of component A.

27. The method of claim 17, wherein the proportion of oxygen is about 2–50 mole percent based on total oxygen and carbon monoxide.

28. The method of claim 17, wherein a pressure in the range of about 1–500 atm and a temperature in the range of about 60–150° C. are maintained.

29. A method for preparing diphenyl carbonate which comprises contacting phenol with oxygen and carbon monoxide in the presence of an amount effective for carbonylation of at least one catalytic material comprising the following and any reaction products thereof:
(A) palladium(II) 2,4-pentanedionate,
(B) at least one tetraalkylammonium bromide or hexaalkylguanidinium bromide, and
(C) at least one lead bromophenoxide.

30. A catalyst composition comprising the following and any reaction products thereof:
(A) Group VIII metal having an atomic number of at least 44 or a compound thereof,
(B) at least one bromide or chloride salt, and
(C) at least one lead haloaryloxide.

31. The composition of claim 30, wherein the haloaryloxide has the formula $$Pb_nO_m(OA)_{(2-z)(n-m)}X_z(n-m), \quad (I)$$
wherein A is an aromatic radical, X is chlorine or bromine, n has a value in the range of 1–3, m has a value in the range of 0–1 and z has a value in the range of 0.1–2.0, with the proviso that the values of n and m cannot be the same.

32. The composition of claim 31, wherein X is bromine.

33. The composition of claim 32, wherein A is unsubstituted phenyl.

34. The composition of claim 32, wherein the Group VIIIB metal in component A is palladium.

35. The composition of claim 34, wherein component A is palladium(II) 2,4-pentanedionate.

36. The composition of claim 32, wherein component B is a bromide salt.

37. The composition of claim 36, wherein component B is a tetraalkylammonium bromide, a tetraalkylphosphonium bromide or a hexaalkylguanidinium bromide.

38. The composition of claim 32, wherein component B is present in the amount of about 1–2,000 equivalents of halide per equivalent of the Group VIII metal of component A and component C in the amount of about 0.2–200 gram-atoms of lead per equivalent of the Group VIII metal of component A.

39. A composition comprising the following and any reaction products thereof:

(A) palladium(II) 2,4-pentanedionate,
(B) at least one tetraalkylammonium bromide or hexaalkylguanidinium bromide, and
(C) at least one lead bromophenoxide.

* * * * *